United States Patent
Duysens et al.

(10) Patent No.: US 6,308,105 B1
(45) Date of Patent: Oct. 23, 2001

(54) MEDICAL ELECTRICAL STIMULATION SYSTEM USING AN ELECTRODE ASSEMBLY HAVING OPPOSING SEMI-CIRCULAR ARMS

(75) Inventors: Victor P.J. Duysens, Ba Grevenbicht; Leo Kretzers, Bj Sittard; Paulus Van Venrooij, Ez Hoensbroek; Paulus A. A. Gubbels, At Brunssum; Paulus G. Adams, Er Munstergeleen, all of (NL)

(73) Assignee: Medtronic Inc., Minneapolis, MN (US)

( * ) Notice: Subject to any disclaimer, the term of this patent is extended or adjusted under 35 U.S.C. 154(b) by 0 days.

(21) Appl. No.: 09/353,621

(22) Filed: Jul. 15, 1999

(51) Int. Cl.⁷ .................................................. A61N 1/05

(52) U.S. Cl. ............................... 607/118; 607/116

(58) Field of Search .................... 607/116, 118; 600/377

(56) References Cited

U.S. PATENT DOCUMENTS

| | | | | |
|---|---|---|---|---|
| 4,920,979 | * | 5/1990 | Bullara | 607/118 |
| 5,095,905 | * | 3/1992 | Klepinski | 600/377 |
| 5,215,089 | * | 6/1993 | Baker, Jr. | 600/377 |
| 5,375,594 | * | 12/1994 | Cueva | 607/118 |

FOREIGN PATENT DOCUMENTS

WO 91/17791-A1 * 11/1991 (WO) ................................ 607/118

* cited by examiner

Primary Examiner—Carl Layno
(74) Attorney, Agent, or Firm—Thomas F. Woods; Michael J. Jaro; Tom G. Berry

(57) ABSTRACT

A system for providing electrical stimulation to the trigeminal nerve through a lead. The lead features a lead body, a coupling for connecting a lead into a medical stimulator and a distal electrode assembly. The electrode assembly features a pair of oppositely disposed curved semi-circular cuffs disposed to conform a lumen therethrough. The ends of each cuff are mounted into a resilient hinge disposed upon the distal end of the lead body. The hinge biases the cuffs towards one another in such a manner that the lumen is maintained patent such that the nerve will remain therein. The hinge is further designed so as to be easily opened so as to spread the cuffs apart. Hinge opening is accomplished through a specialized implant tool, the implant tool being a generally cylindrical tube designed to meet about the lead body. A divergence in the lead body near the hinge permits the implant tool to engage the lead body in that section and thus forces the cuffs apart. In such a manner the cuffs may be opened so as to be implanted around the lead merely through manipulation of the proximal end of the lead body. Thus, this design permits the leads to be implanted using the so-called "key-hole" surgical approach. Additional embodiments of the lead are also disclosed.

10 Claims, 7 Drawing Sheets

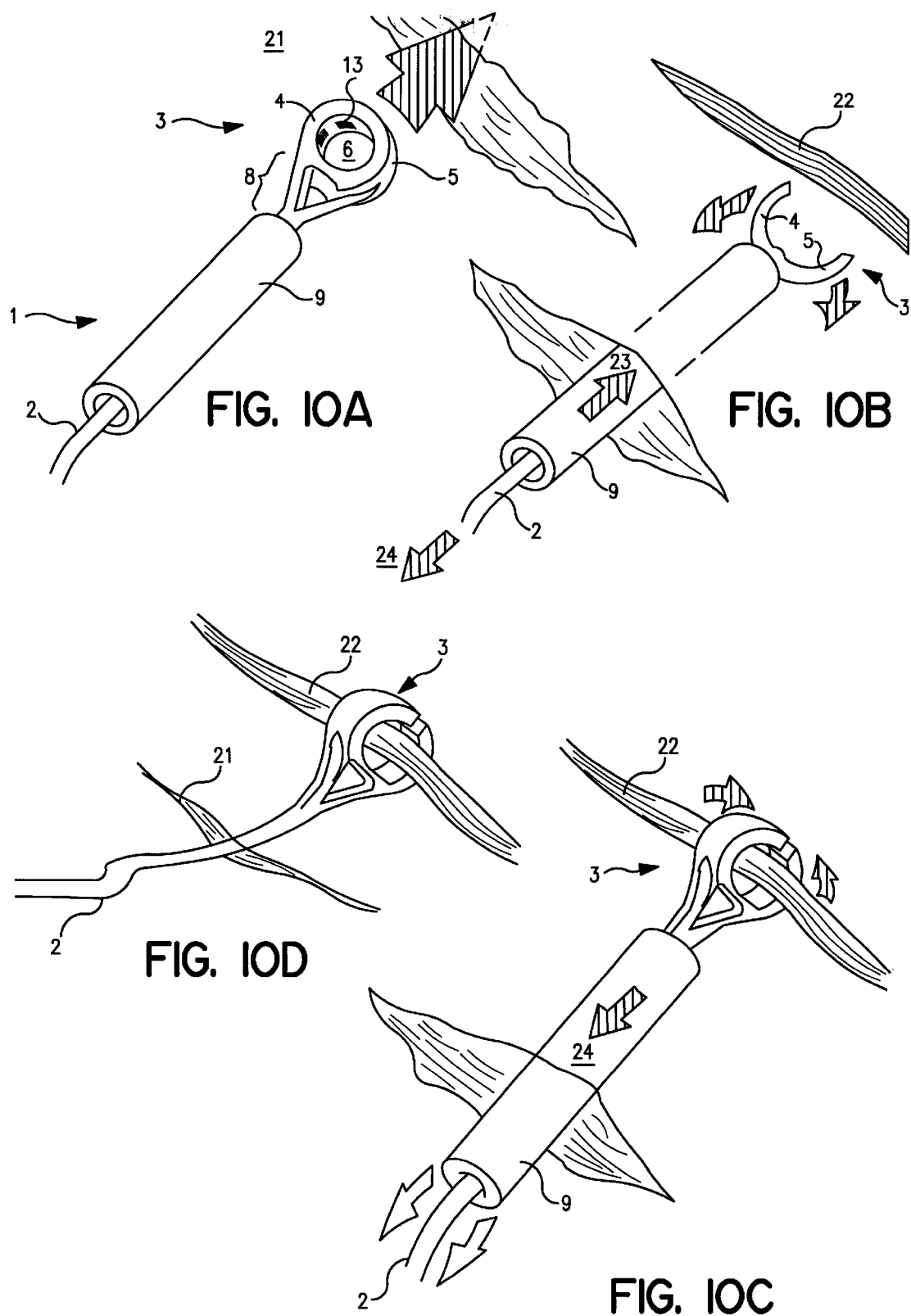

MEDICAL ELECTRICAL STIMULATION SYSTEM USING AN ELECTRODE ASSEMBLY HAVING OPPOSING SEMI-CIRCULAR ARMS

FIELD OF THE INVENTION

The present invention relates to medical electrical stimulation, and particularly to a system to provide medical electrical stimulation to nervous tissue.

BACKGROUND OF THE INVENTION

Medical electrical stimulation is currently used for a variety of reasons. Among the fastest growing indications for medical electrical stimulation is the treatment or suppression of pain.

Medical electrical stimulation typically treats pain through the application of electrical pulses to a nerve or nerve fibers. Generally speaking, one of the difficulties with providing electrical stimulation to nerve fibers is to provide an adequate, simple and reliable coupling of the treatment electrodes with the nerve fibers.

One nerve which may be in need of electrical stimulation to treat pain is the trigeminal nerve. The trigeminal nerve is the largest of the facial nerves.

Trigeminal neuralgia is a malfunction of this nerve which causes (usually) spasmodic pain. Any of the three branches can be affected. The pain can be caused by one or more of several causes.

Pressure of a blood vessel on the root of the nerve.

Demyelinization of the nerve (i.e. the destruction of the myelin sheath that protects the nerve fiber).

Physical damage, such as failed dental procedures or infections.

Unknown. Not all cases seem to have a clear cause.

Only one side of the face is usually affected, but trigeminal neuralgia of both sides is also known to exist. In "classical" trigeminal neuralgia, the pain is extremely sharp and seizure-like. It is often triggered by certain stimuli such as touching the face, eating, talking, shaving, etc. These triggers vary from person to person.

When a blood vessel is suspected to be pressing on the root entry zone, an operation, aimed at removing the source of the compression, requires a craniotomy at the base of the skull. This bony opening is often very small, referred to as "key hole" surgery.

Symptom relief is usually obtained through microvascular compression where offending blood vessel is physically moved away from the root entry zone. On occasion, a more radical approach is required such as partial or complete cutting of the nerve. This procedure is very effective and long lasting, particularly if an artery is found compressing the nerve as it enters the brainstem.

Common complications from rhizotomy procedures include facial or eye numbness, change in bite and TMJ problems. Serious complications such as strole, paralysis, blindness or death are rare. The typical complications of microsurgical vascular decompression are facial or eye numbness, deafness, coordination problems, change in bite, TMJ problems and wound healing problems.

One of the typical features of trigeminal neuralgia is that it is rarely typical. In addition to the stabbing neuralgic pain, many victims experience various kinds of pain that may be described as burning, crushing, pulsating, etc. These "typical" forms of pain are often very difficult to treat.

Trigeminal neuralgia is a very rare condition. Statistics vary, but the relevance is probably about 150 cases per million people per year. There are some relatively effective treatments for trigeminal neuralgia. Unfortunately, although some of the treatments are becoming standard, there is no single treatment that is effective for all victims.

In a so-called "key-hole" surgical operation the neurosurgeon approaches the point where the trigeminal nerve enters the brain (the root entry zone) directly, using an operating microscope, through a small opening behind the car at the affected side. The surgeon searches for, and nearly always finds, a blood vessel (usually an artery, but it could be a vein) close against the nerve, kinking the nerve. It is presumed that the physical kinking of the nerve by the offending blood vessel has a part to play in causing trigeminal neuralgia. The vessel is carefully separated from the nerve thus unkinking or decompressing the nerve. It is important to be sure that the separation of the vessel and nerve is maintained so as to reduce the chance of the condition recurring. For this purpose teflon cotton pads are placed in between the vessel and the nerve. Often, however, separation of the nerve and vessel is not sufficient and electrical stimulation is desired to suppress pain.

SUMMARY OF THE INVENTION

Thus, there exists a need for a medical electrical lead configured for implant around a trigeminal nerve.

There exists a further need for such a lead which is suitable for implant through the so-called "key-hole" surgical approach.

These and other needs are met by the present invention, which provides a system for providing electrical stimulation to the trigeminal nerve through a novel lead. The lead features a lead body, a coupling for connecting a lead into a medical stimulator and a distal electrode assembly.

The electrode assembly features a pair of oppositely disposed curved semi-circular cuffs disposed to conform a lumen therethrough. The ends of each cuff are mounted into a resilient hinge disposed upon the distal end of the lead body. The hinge biases the cuffs towards one another in such a manner that the lumen is maintained patent such that the nerve will remain therein. The hinge is further designed so as to be easily opened so as to spread the cuffs apart. Hinge opening is accomplished through a specialized implant tool, the implant tool being a generally cylindrical tube designed to meet about the lead body. A divergence in the lead body near the hinge permits the implant tool to engage the lead body in that section and thus forces the cuffs apart. In such a manner the cuffs may be opened so as to be implanted around the lead merely through manipulation of the proximal end of the lead body. Thus, this design permits the leads to be implanted using the so-called "key-hole" surgical approach. Additional embodiments of the lead are also disclosed.

BRIEF DESCRIPTION OF THE FIGURES

FIGS. 10A–D disclose the steps used to implant the lead according to the present invention.

DETAILED DESCRIPTION OF THE FIGURES

Figure 1:
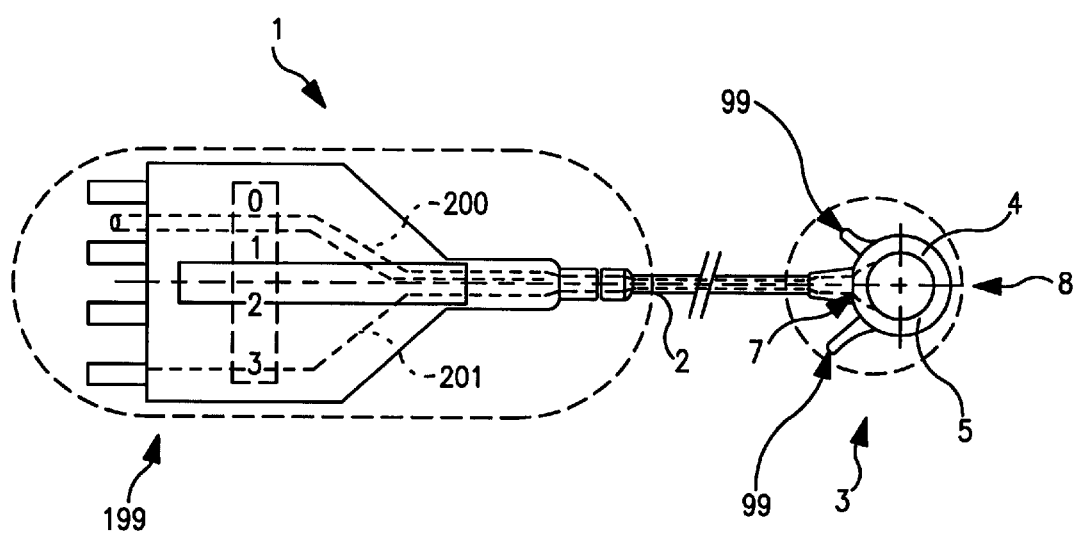
FIG. 1 is a detailed view of the distal end of the present invention.

FIG. 1 is a detailed view of the distal end of the present invention. As seen, the invention generally consists of lead 1 having a lead body 2, a distal electrode assembly 3 and a connector assembly 199. Distal electrode assembly may be constructed according to that already used, such as the flat connector assembly featured in the Medtronic Model 3586 lead. Lead body may, likewise, be constructed similar to that already used in the Medtronic Model 3586 lead and preferably would feature a series of elongated conductors 201 covered by an insulator such as a silicone rubber having a hardness of 65–78 on the shore A scale. Lead may be coupled to a medical electrical stimulator, such as the Medtronic Itrel II. Lead may also be coupled to a combination electrical stimulator and drug pump. The lead, in this instance, will also feature one or more drug delivery passages 200 to deliver drugs from proximal end of lead to the distal end, preferably adjacent electrodes. As shown, the distal electrode assembly 3 features a pair of oppositely disposed curved cuffs 4 and 5. One or more electrodes may be disposed upon each of the cuffs. Electrodes would preferably be constructed of a platinum/iridium alloy and would be coupled to the electrical conductors disposed within the lead body 2. Each cuff, further, features a grip 99, the grips ultimately being oppositely disposed and, thus, providing a surface which may be gripped or pinched together to thereby spread apart the two opposing cuffs and provide access to the lumen therein.

Figure 2B:
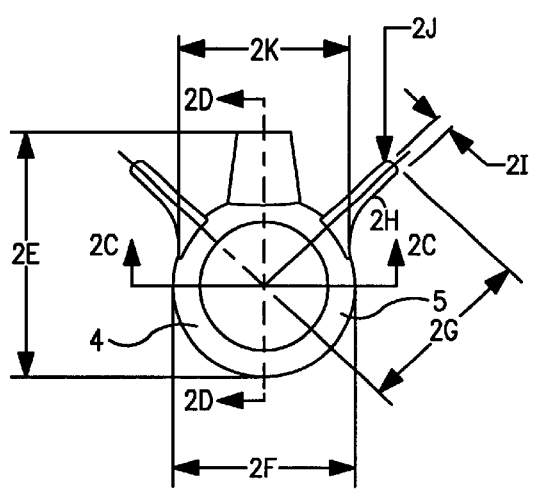
FIG. 2B is an end view showing the side of the distal electrode assembly.
Figure 2D:
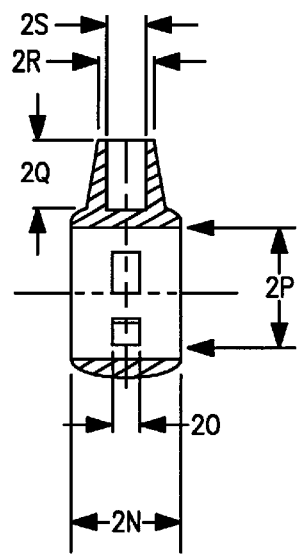
FIG. 2D is a sectional view taken along the line FIG. 2D—2D of FIG. 2B.
Figure 2C:
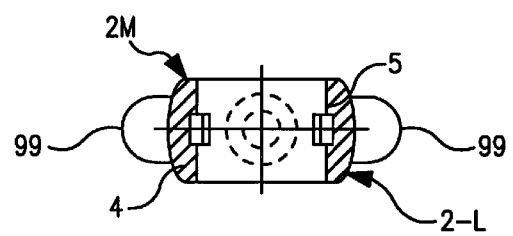
FIG. 2C is a sectional view taken along the line FIG. 2C—2C of FIG. 2B.
Figure 2A:
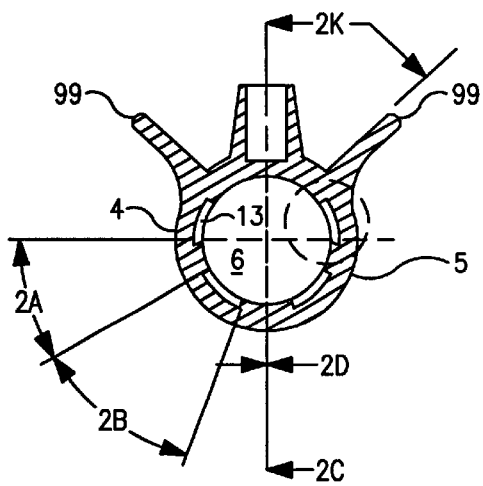
FIG. 2A is a sectional view of the distal electrode assembly.

FIG. 2A is a sectional view of the distal electrode assembly 3.

FIG. 2B is an end view showing the side of the distal electrode assembly 3.

FIG. 2C is a sectional view taken along the line FIG. 2C—2C of FIG. 2B.

FIG. 2D is a sectional view taken along the line FIG. 2D—2D of FIG. 2B.

Figure 2E:
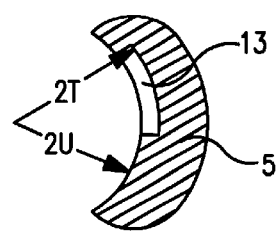
FIG. 2E is a detailed view showing the electrode recess within a cuff.

FIG. 2E is a detailed view showing the electrode recess within a cuff. These views show several salient features and corresponding dimensions used by the preferred embodiment. They are, thus, alternatives of one lead which may be constructed according to the present invention and should not be interpreted as a limitation on the scope of the invention.

| REFERENCE NUMBER | DIMENSION |
|---|---|
| 2-A | 27.5° |
| 2-B | 40° |
| 2-C | 18.8° |
| 2-D | Maximum of 0.15 m |
| 2-E | 7 mm |
| 2-F | 5 mm diameter |
| 2-G | 5 mm |
| 2-H | 2 mm round |
| 2-I | 0.5 mm |
| 2-J | 0.25 mm radius |
| 2-K | 45° |
| 2-L | 2.75 mm radius spherical |
| 2-M | 0.1 mm radius |
| 2-N | 3 mm |
| 2-O | 0.7 mm |
| 2-P | 3.5 mm diameter |
| 2-Q | 2 mm |
| 2-R | 1.5 mm |
| 2-S | 1.05 mm |
| 2-T | 1.95 mm radius |
| 2-U | 1.75 mm radius |

Figures 3, 6:
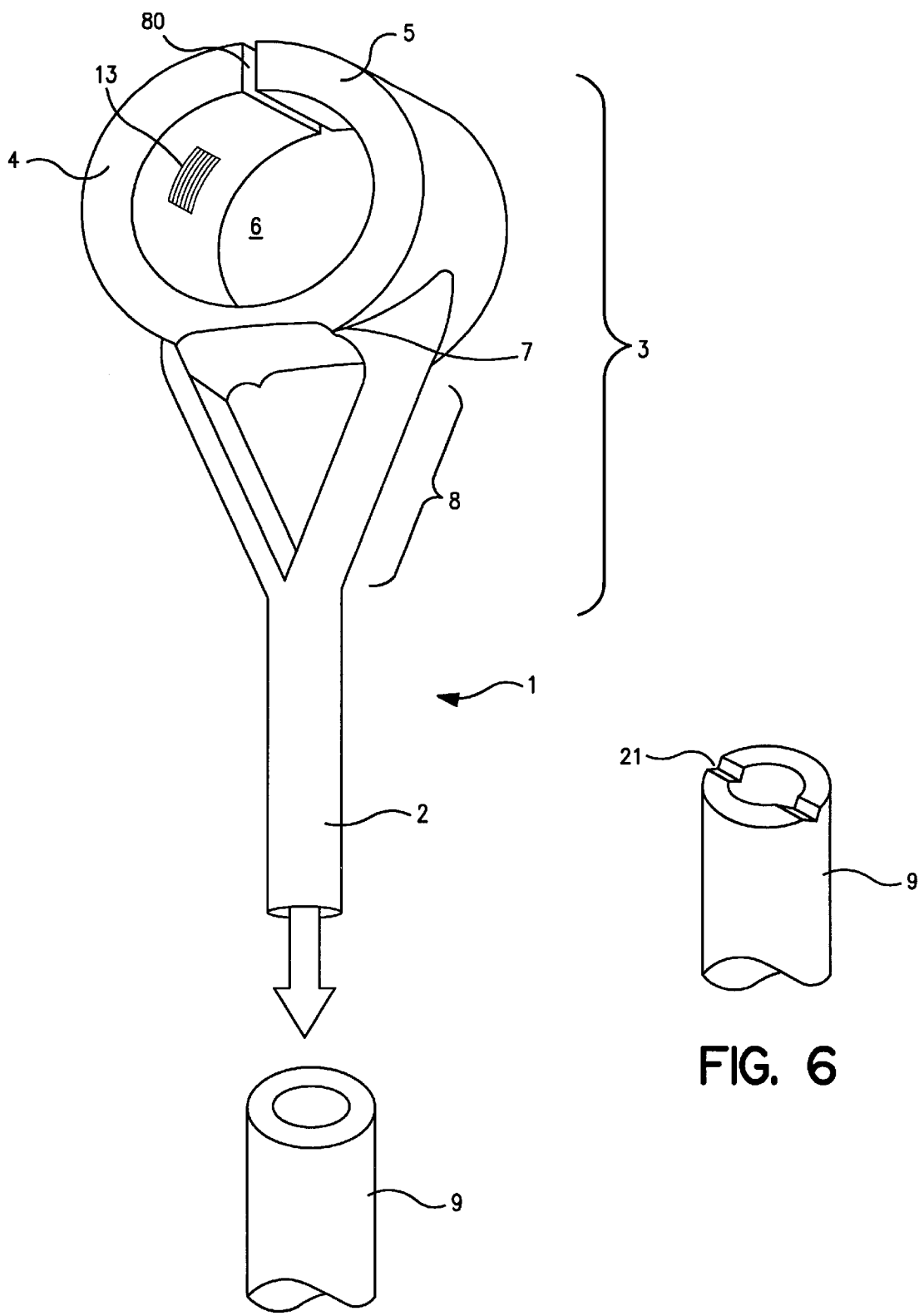
FIG. 3 is a detailed view of the distal end of an alternative embodiment of the present invention.
FIG. 6 shows an alternative embodiment of the implant tool.

FIG. 3 is a detailed view of the distal end of an alternative embodiment of the present invention. As seen, the present invention generally consists of a lead 1 having a lead body 2 and a distal electrode assembly 3. The distal electrode assembly itself features a pair of oppositely disposed curved cuffs 4 and 5. One or more electrodes 13 may be provided upon each of the cuffs 4 and 5. Electrodes preferably are constructed of platinum/iridium alloy and are coupled to the electrical conductors disposed within lead body 2. The cuffs define a lumen 6 therein. The cuffs are mounted to a resilient hinge 7 at one end. The cuffs are not mounted at the other ends and instead provide a relatively minor through-between 80. The hinge is provided so as to permit the cuffs to be spread apart such that a nerve may be introduced into the lumen 6 merely by manipulation of the lead at the proximal end. As discussed above, this is a requirement to implant the lead using the so-called "key-hole" approach.

The present invention provides this functionality through the co-operation of the divergent lead body 8 and the implant tool 9. This is best seen in FIGS. 2 and 3.

Figure 4:
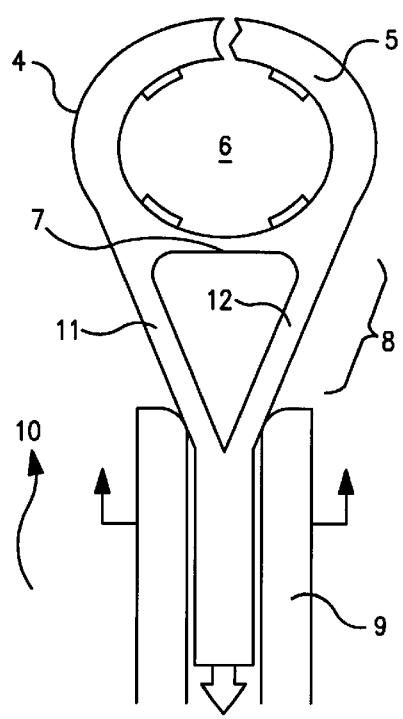
FIGS. 4 and 5 is a sectional view of an alternative embodiment of the lead and implant tool.
Figure 5:
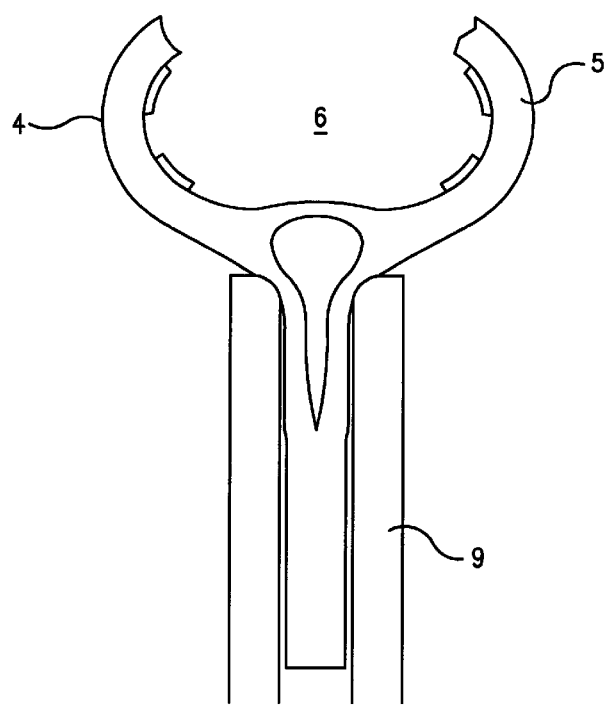

FIG. 4 is a sectional view of the lead and implant tool. As can be seen, movement of the implant tool 9 in the direction 10 causes the divergent lead body 8 and, in particular, the first member 11 of the divergent lead body and second member 12 of the divergent lead body to be pushed together thereby causing the hinge 7 to open and, thus, spread cuffs 4 and 5 apart. This is best seen in FIG. 3.

Hinge, moreover, is provided so as to bias cuffs 4 and 5 together. Thus, upon movement of implant tool back to its original position, shown in FIG. 2 or that shown in FIG. 4, the cuffs again move back into position until lumen 6 is substantially enclosed by cuffs 4 and 5. In the present invention cuffs, hinge and divergent lead body are provided with the same material, preferably silicone rubber having a 65–78, shore A hardness.

FIG. 6 shows an alternative embodiment of the implant tool. In this embodiment implant tool 9 has a pair of oppositely disposed notches 21 particularly designed to engage the members of divergent lead body 8.

Figure 9:
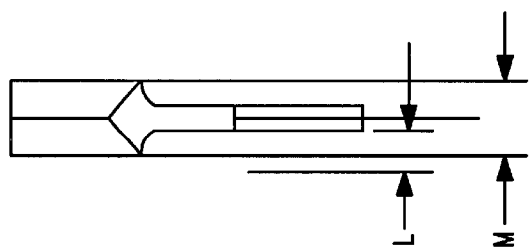
FIG. 9 is an orthogonal side view shown in FIGS. 7 and 8.
Figure 8:
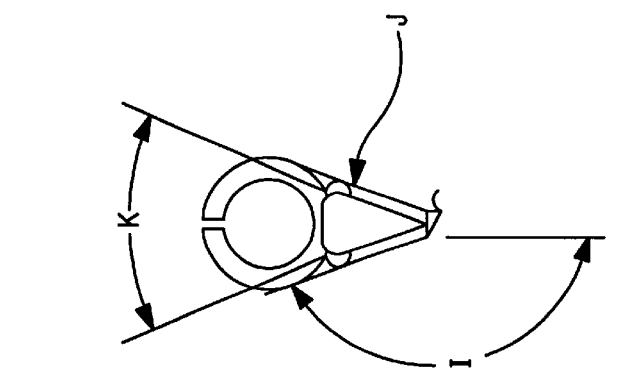
FIG. 8 is a further side view showing additional dimensions of the present invention.
Figure 7:
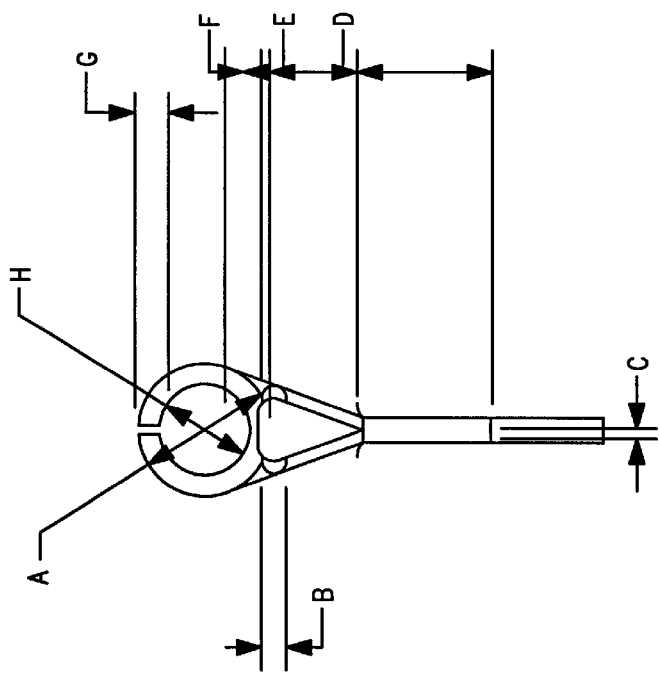
FIG. 7 is a side view showing additional dimensions of the distal end of an alternative embodiment of the present invention.

FIGS. 7, 8 and 9 depict the salient dimensions for the embodiment shown in FIG. 3.

FIG. 7 is a side view showing the lumen in the cuffs.

FIG. 8. is a further side view showing additional radial dimensions.

FIG. 9 is an orthogonal side view shown in FIGS. 7 and 8. They are, thus, alternatives of one lead which may be constructed according to the present invention and should not be interpreted as a limitation on the scope of the invention.

| REFERENCE NUMBER | DIMENSION |
|---|---|
| A | 5 mm diameter |
| B | 0.75 radius |
| C | 0.5 |
| D | 5 |
| E | 3.75 |
| F | 1.64 |
| G | 1.14 |
| H | 3.5 diameter |
| I | 159.73° |
| J | 0.51 radius |
| K | 43.14° |
| L | 1.5 |
| M | 3 |

FIGS. 10A–D disclose the steps used to implant the lead according to the present invention. As seen in FIG. 10A an incision 21 has been made providing access to a nerve. At this point the lead may be inserted into the incision so as to approach the exposed nerve.

At FIG. 10B as a lead approaches the nerve, seen here as 22, the distal electrode assembly is opened. This is accomplished through the relative movement of the implant tool in the direction opposite to the movement of the lead body. These are indicated through opposing, arrows 23 and 24. As can be appreciated by comparison of FIG. 10A and FIG. 10B the movement of tool opposite to lead body causes the distal surface of tool to engage the divergent lead body thereby causing the hinge and cuffs to open.

Next, turning to FIG. 10C, once the distal electrode assembly 3 is positioned so as to envelop the nerve, the implant tool is moved in the opposite direction, shown here as arrow 24. This ultimately causes the release of the divergent lead body. Due to the resilience of members as well as the hinge, the cuffs are again moved back to their original positions so as to envelop nerve 22 in lumen 6.

Finally, referring to FIG. 10D the implant tool is removed. Thereafter the incision may be closed and medical electrical stimulation may be provided to the nerve.

Figure 11:
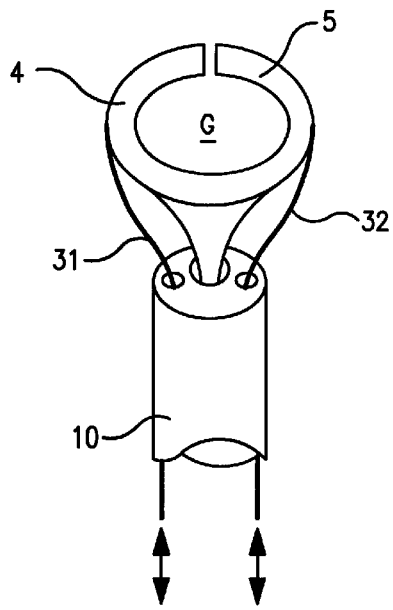
FIG. 11 shows an alternative embodiment to the present invention.

FIG. 11 shows an alternative embodiment to the present invention. In this embodiment the implant tool comprises a cylinder 10 which features two or more wires 31 and 32. The wires are mounted to the cuffs 4 and 5. In such a manner pulling on the wire causes cuffs to move and thereby open lumen 6.

Figure 13:
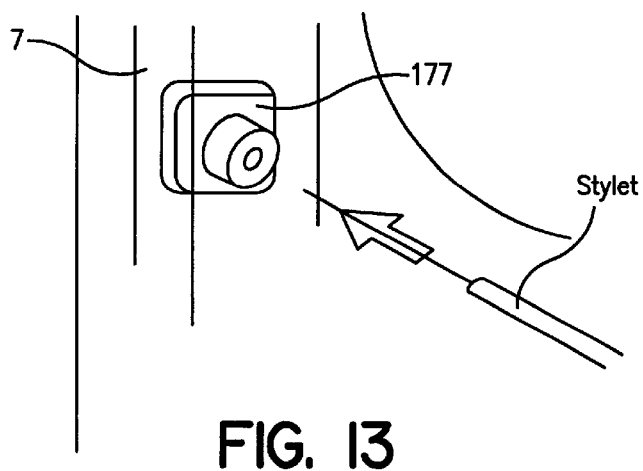
FIG. 13 shows a detail for the stylet engagement member used in FIG. 12.
Figure 12:
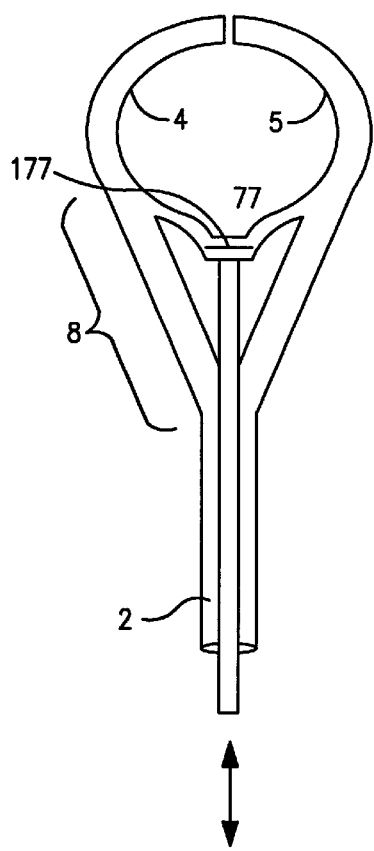
FIG. 12 shows a further alternative embodiment.

FIG. 12 shows a further alternative embodiment. In this embodiment a stylet is used to spread the cuffs apart. As seen, stylet is introduced within lead body 2 such that it butts against hinge 7. Movement of stylet further against hinge 7 will cause the cuffs to spread apart in the manner already discussed above. As further seen, a stylet engagement member 177 is provided to dissipate stress from stylet. Member 177 is preferably metal and is shown in detail in FIG. 13.

What is claimed is:

1. A system for providing medical therapy comprising:
a lead comprising a lead body and an electrode assembly, the electrode assembly having two opposing semi-circular arms forming a lumen therethrough, the arms being mounted on a resilient hinge, the hinge comprising means for spreading the arms apart, wherein the arm spreading means comprises a pair of oppositely disposed grips, the grips comprising a surface which may be gripped by the fingers of a user to spread apart the two opposing semi-circular arms and provide access to the lumen.

2. A system for providing medical therapy comprising:
a lead comprising a lead body and an electrode assembly, the electrode assembly having two opposing semi-circular arms forming a lumen therethrough, the arms being mounted on a resilient hinge, the hinge comprising means for spreading the arms apart,
an implant tool disposed with the lead body, the implant tool comprising a first surface configured to engage the hinge and spread the arms apart; the implant tool comprising a stylet.

3. A system for providing medical therapy comprising:
a lead comprising a lead body and an electrode assembly, the electrode assembly having two opposing semi-circular arms forming a lumen therethrough, the arms being mounted to a resilient hinge, the hinge having means for opening the arms apart;
an implant tool disposed with the lead body, the implant tool comprising a first surface configured to engage the hinge and spread the arms apart, the implant tool comprising a stylet, a stylet engagement member being disposed with the hinge and configured to receive a portion of the stylet.

4. A system for providing medical therapy comprising:
a lead comprising a lead body and an electrode assembly, the electrode assembly having two opposing semi-circular arms forming a lumen therethrough, the arms being mounted on a resilient hinge, the hinge comprising means for spreading the arms apart, an implant tool being disposed with the lead body and comprising a first surface configured to engage the hinge and spread the arms apart, the implant tool comprising a hollow cylinder disposed around the lead body, a distal end of the cylinder being configured to engage the hinge and spread the arms apart.

5. A system for providing medical therapy comprising:
a lead comprising a lead body and an electrode assembly, the electrode assembly having two opposing semi-circular arms forming a lumen therethrough, the arms being mounted on a resilient hinge, the hinge comprising means for spreading the arms apart; and
a drug pump coupled to the lead.

6. A system for providing medical therapy comprising:
a lead body comprising means for coupling the lead to an electrical stimulator, an elongated electrical conductor, an elongated insulative sheath for electrically insulating the elongated electrical conductor, and a resilient hinge disposed near a distal end of the lead body;
a first curved cuff operably connected to the hinge;
an electrode disposed on the first cuff, the electrode being electrically connected to the elongated conductor;
a second curved cuff operably connected to the hinge, and
wherein in a closed position the hinge biases the first curved cuff towards the second curved cuff, the hinge further comprising means for spreading the first cuff apart from the second cuff so that the hinge assumes an open position;
wherein the spreading means further comprises a divergent lead body and an implant tool disposed around a portion of the lead body, the implant tool comprising a first surface configured to engage the hinge and spread the first and second cuffs apart.

7. A system for providing medical therapy comprising:
a lead body comprising means for coupling the lead to an electrical stimulator, an elongated electrical conductor, an elongated insulative sheath for electrically insulating the elongated electrical conductor, and a resilient hinge disposed near a distal end of the lead body;
a first curved cuff operably connected to the hinge;
an electrode disposed on the first cuff, the electrode being electrically connected to the elongated conductor, and
a second curved cuff operably connected to the hinge;
wherein in a closed position the hinge biases the first curved cuff towards the second curved cuff, the hinge further comprising means for spreading the first cuff apart from the second cuff so that the hinge assumes an open position, and the implant tool is a cylindrical rod, a first end of the rod having a notch configured to engage the divergent lead body.

8. A system according to claim 7, wherein the spreading means further comprises a pair of oppositely disposed grips, the grips comprising a surface which may be gripped by the fingers of a user to spread apart the two opposing semicircular arms and provide access to the lumen.

9. A system for providing medical therapy, comprising:
a lead body comprising means for coupling the lead to an electrical stimulator, an elongated electrical conductor, an elongated insulative sheath for electrically insulating the elongated electrical conductor, and a resilient hinge disposed near a distal end of the lead body;
a first curved cuff operably connected to the hinge;
an electrode disposed on the first cuff, the electrode being electrically connected to the elongated conductor;
a second curved cuff operably connected to the hinge, and
means for delivering a fluid through the first curved cuff;
wherein in a closed position the hinge biases the first curved cuff towards the second curved cuff, the hinge further comprising means for spreading the first cuff apart from the second cuff so that the hinge assumes an open position.

10. A system according to claim 9, wherein the means for delivering a fluid through the first curved cuff further comprises means for delivering the fluid to a location near the electrode.

* * * * *